United States Patent [19]
Smart

[11] Patent Number: 6,031,371
[45] Date of Patent: Feb. 29, 2000

[54] SELF-POWERED PIPELINE VEHICLE FOR CARRYING OUT AN OPERATION ON A PIPELINE AND METHOD

[75] Inventor: Andrew Smart, Loughborough, United Kingdom

[73] Assignee: BG plc, Berkshire, United Kingdom

[21] Appl. No.: 08/952,115

[22] PCT Filed: May 21, 1996

[86] PCT No.: PCT/GB96/01214

§ 371 Date: Mar. 23, 1998

§ 102(e) Date: Mar. 23, 1998

[87] PCT Pub. No.: WO96/37727

PCT Pub. Date: Nov. 28, 1996

[30] Foreign Application Priority Data

May 22, 1995 [GB] United Kingdom ................... 9510434

[51] Int. Cl.[7] .............................. F16L 55/26; F16L 55/18; G01N 27/72
[52] U.S. Cl. .............................. 324/220; 138/97; 166/55; 166/55.7; 324/226
[58] Field of Search .................................... 324/219–221, 324/226, 262; 73/40.5, 623; 15/104.05, 104.063, 104.09; 165/11.2; 166/55, 55.7, 55.8; 138/97

[56] References Cited

U.S. PATENT DOCUMENTS

| | | |
|---|---|---|
| 3,238,448 | 3/1966 | Wood et al. ............................ 324/220 |
| 3,949,292 | 4/1976 | Beaver et al. ........................... 324/220 |
| 4,050,384 | 9/1977 | Chapman ............................ 324/220 X |
| 4,443,948 | 4/1984 | Reeves . |
| 4,447,777 | 5/1984 | Sharp et al. ............................. 324/220 |
| 4,481,816 | 11/1984 | Prentice . |
| 4,581,938 | 4/1986 | Wentzell ................................... 73/623 |
| 4,852,391 | 8/1989 | Ruch et al. ............................... 73/40.5 |
| 4,986,314 | 1/1991 | Himmler ................................ 166/55.7 |
| 5,025,215 | 6/1991 | Pirl ........................................ 324/220 |
| 5,197,540 | 3/1993 | Yagi et al. ............................. 166/55.8 |
| 5,313,838 | 5/1994 | Gondard et al. .................... 324/220 X |
| 5,396,800 | 3/1995 | Drinon et al. ............................ 73/623 |

FOREIGN PATENT DOCUMENTS

4024926 2/1992 Germany .

*Primary Examiner*—Gerard Strecker
*Attorney, Agent, or Firm*—Oblon, Spivak, McClelland, Maier & Neustadt, P.C.

[57] ABSTRACT

An in-pipe vehicle for carrying out at least one operation in a pipeline. The vehicle includes a train of modules interlinked by suspension units to allow serpentine movement through pipe bends. The vehicle train has its own internal power supply and drive mechanism in the modules. A detector module determines the presence of a service junction using magnetic field information. A manipulative module allows the vehicle to be temporarily wedged in the pipeline while providing rotational movement to facilitate the desired operation at the junction. This may include drilling and welding of a service pipe to the main using appropriate modules. A remote probe typically containing a magnetic field generator can be used to assist in service junction location by the vehicle.

30 Claims, 8 Drawing Sheets

SELF-POWERED PIPELINE VEHICLE FOR CARRYING OUT AN OPERATION ON A PIPELINE AND METHOD

BACKGROUND OF THE INVENTION

1. Field of the Invention

The invention relates to an in-pipe vehicle which can carry out an operation within a pipeline, which pipeline may be a gas carrying pipeline.

2. Discussion of the Background

There have been various activities undertaken concerned with pipeline inspection including remote cameras to enable information on the internal condition of pipelines to be obtained.

SUMMARY OF THE INVENTION

The present invention is concerned generally with an arrangement which will allow operations to be undertaken from within the pipeline, without the need for external drives, umbilicals or other connections which restrict the movement or utility of such arrangements.

According to the invention there is provided a pipeline vehicle comprising a plurality of linked modules forming a powered train for travelling within a pipeline, at least one of the modules being capable of carrying out an operation on the pipeline, and wherein a module includes clamping means for holding the vehicle at a fixed point in the pipeline whilst rotational means are operable to rotate part or parts of the vehicle to align the module capable of carrying out the operation.

Further according to the invention there is provided a method of effecting an operation on a pipeline comprising passing a vehicle consisting of a train of modules through the pipeline to detect the presence of an item to be operated on; moving the vehicle to align a module with the item to carry out the desired operation, the alignment step including clamping the vehicle and effecting axial movement of the module.

Further according to the invention there is provided a pipeline vehicle having a generally cylindrical body portion and including detector means for detecting the presence of a pipe junction in a main pipeline, means for forming an aperture in a liner within the main pipeline, and means for axially rotating the body portion to align the aperture forming means with the pipe junction prior to forming the aperture at the pipe junction.

Still further according to the invention there is provided a flexible probe for indicating the proximity of an auxiliary pipe to a device within the main pipe said probe including means for generating a magnetic field for detection by the device within the main pipe and indicator means for generating a signal when the probe is adjacent the main pipe.

BRIEF DESCRIPTION OF THE DRAWINGS

The invention will now be described by way of example with reference to the accompanying drawings in which.

DISCUSSION OF THE PREFERRED EMBODIMENTS

Figure 1:
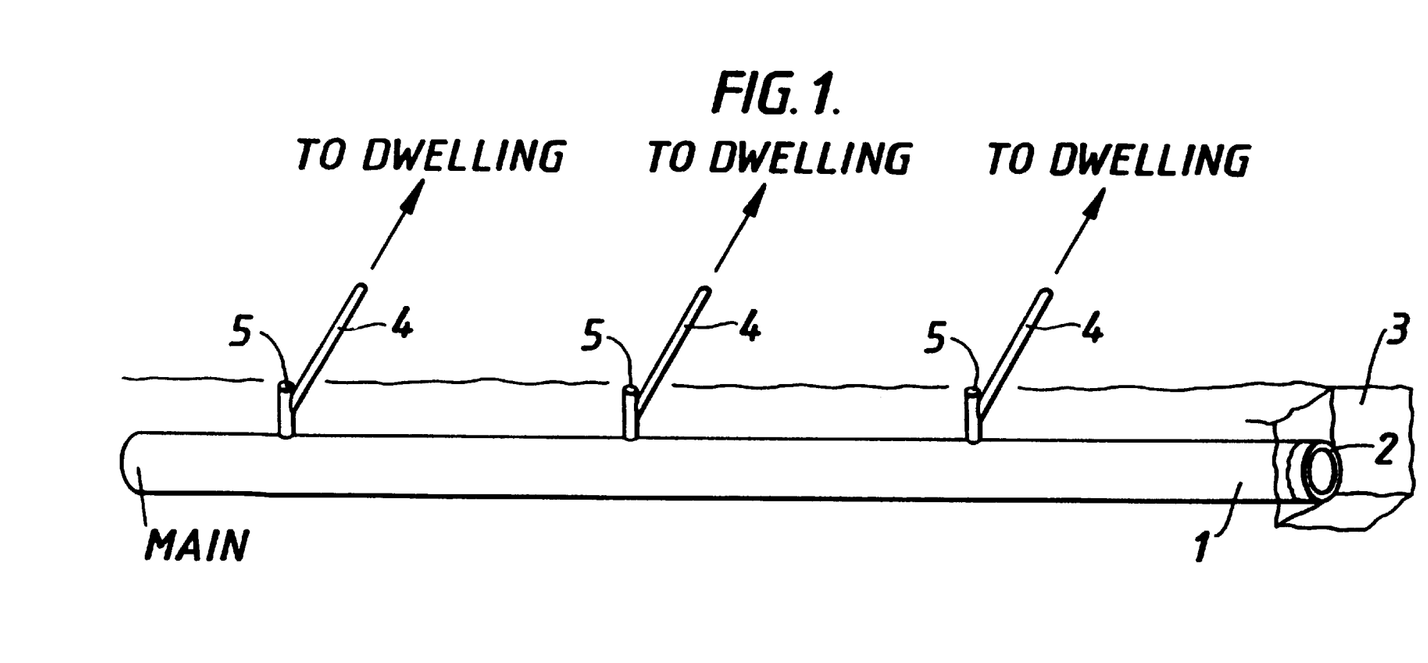
FIG. 1 shows a main pipeline with a number of service take-offs.

A buried cast iron gas main pipeline 1 shown in FIG. 1 carries a polyethylene pipe liner 2 which has previously been inserted through excavation 3 as part of a refurbishment programme.

A number of existing service pipe take-offs 4 each provide the source of gas to individual dwellings or other premises. As part of the refurbishment programme, there is a need to insert a liner in each service pipe and to join this to the main liner 2. In order to achieve this it has been necessary in the past to make an excavation at each service connection 5 (e.g. a screwed pipe connector or a service tee) and penetrate the main liner 2 through the excavation, sealing the take off to the main using a saddle connection, having removed part of the cast iron main in that region.

Figure 2:
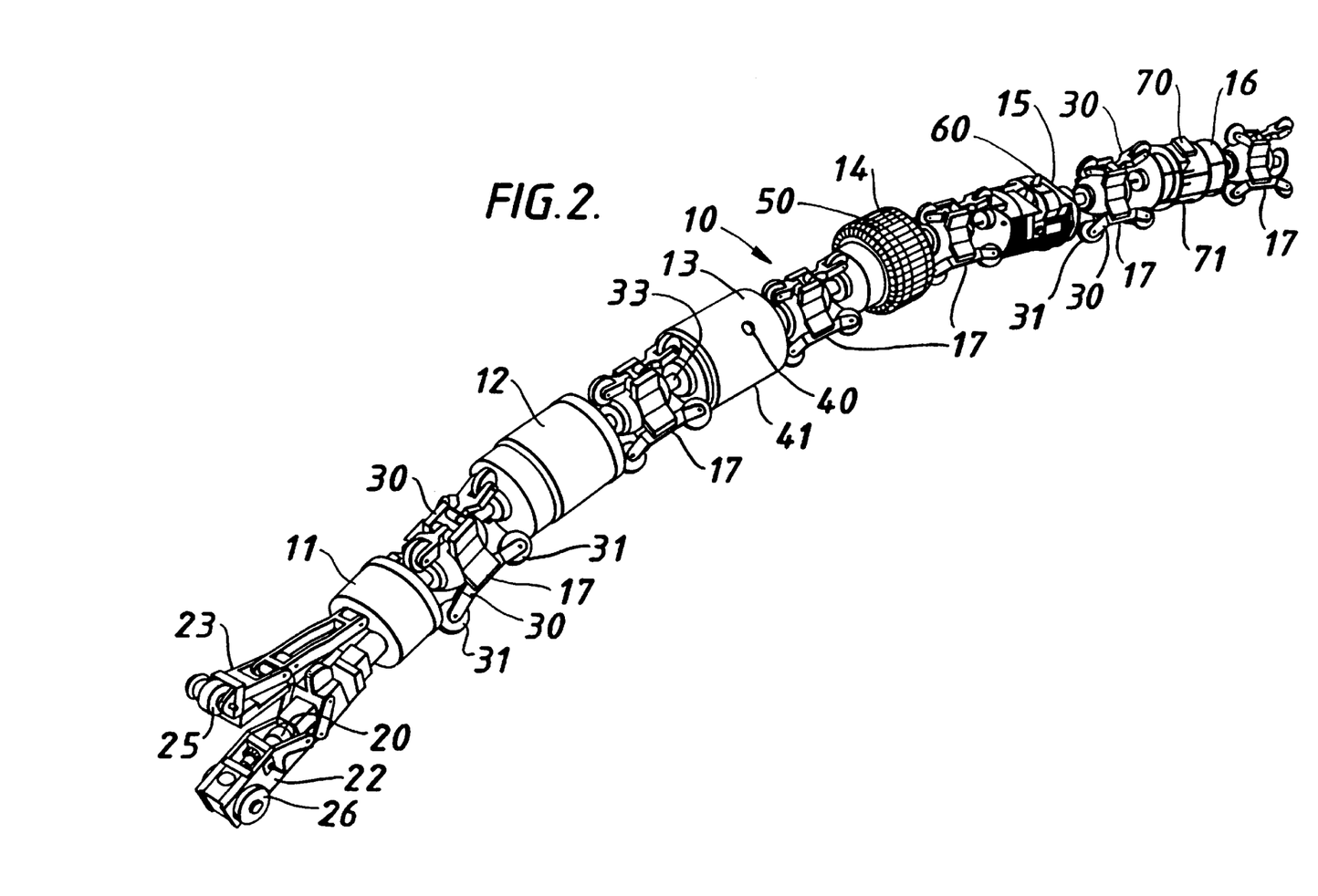
FIG. 2 shows an embodiment of the self-powered pipeline vehicle comprising a number of modules.

In the present invention, the need to have individual excavations is avoided as is the need to remove portions of the cast iron main at such excavations. FIG. 2 shows the mechanism now employed.

The self-powered in-pipe vehicle 10 of FIG. 2 includes a plurality of dissimilar individual modules 11–16 linked via similar linkage and suspension modules 17. The train of modular elements allows flexibility of operation in that each module provides a specific function which in this embodiment work together to remotely connect polyethylene gas main to service piping inserted into old metal piping (as described below). Other modular configurations would allow further tasks to be effected. The modular arrangement together with the suspension modules allows the degree of serpentine operation needed to negotiate bends in the pipe and to cope with the small diameter of the pipe which can be less than 150 mm.

The first module in the train is the traction module 11 which includes a motor 20 within one of the arms 22, 23 terminating in drive wheels 26 and idler wheels 25 respectively. The moveable arms 22 and 23 allow the wheels to contact closely the inner wall of the pipe through which it traverses and sensors within both the idler and drive wheel detect slippage which causes the traction unit to cause the arm to extend further to increase the traction affect. This can be effected by a motor driven ball screw acting on the lever arm to control the transverse load.

The motor 20 drives the wheels via gearing and feedback on movement, direction and slippage which can be compensated by internal control. Typically the traction unit provides a pushing force for the train of 80 N at a speed of 30 mm/s. Power for the modules including the traction module 11 is provided by the power unit 12 which incorporates a number of rechargeable batteries. Electrical connection to the modules is provided via the suspension unit 17 connectors. The suspension units 17 are provided of common construction and placed between each functional module to give the train flexibility required for small pipes. Each module 17 includes three spring loaded arms 30 terminating in wheels 31. In order to avoid the use of highly preloaded suspension springs, the three lever arms at one end are interconnected via a slider. Thus when the body of the suspension unit is depressed below the pipe centre-line the wheels at the top will be pulled away from the wall to provide no resistance to the upward centralising force. A central shaft 33 through each suspension unit is free to rotate relative to the body. Connectors at each end allow electrical connection between all modules to be effected for power and intercommunication requirements.

The manipulator module 13 includes three retractable extenders 40 which are controlled to extend when required beyond the manipulator's cylindrical body 41 so as to firmly support the module as it becomes wedged in the pipe. A motor with associated gearing (e.g. ring gear) and feedback allows the rear portion of manipulator to rotate relative to the front portion and as the modules are all mechanically linked this causes modules connected to the rear of the manipulator to axially rotate within the pipe so that they can be aligned to a certain portion of the pipe to effect a task when required. A 'global' rotational manipulation for all modules has been found effective rather than each module making adjustments themselves, although 'local' manipulation may be required in addition for a given module. The rotational manipulation can provide two 210° arcs with the body clamped against the pipe wall. Electrical connection through the rotating interface within the manipulator is provided by use of a coiled cable to avoid slip ring interference and reduce module length.

The sensor module 14 includes a number of magnetic sensors 50 spaced around the periphery of the module for detecting a magnetic field from a source which is typically within the module 14. The sensors (typically 40 in number) form part of a variable reluctance magnetic circuit. The detectors can be of the Hall effect type.

As the vehicle moves into the region of a service pipe junction there will be a change in the magnetic field measurement. The hole in the offtake corresponds to the largest loss and indicates its position.

The drill module 15 includes a motorised drill bit 60 capable of drilling a hole through the pipe, but more typically through the pipe liner. A 16mm hole would be suitable to access a 25 mm service pipe tee.

The fusion module 16 carries a sensor 70 (e.g. a force sensor with variable resistance when contacted by a guide wire) for detecting the guide wire in the service pipe liner (for reasons described below) and a heater device 71 for effecting a seal between the main liner and the service pipe liner. The manipulator module 13 allows the rotation by 180° of the train including module 16 to allow the sensing and sealing functions to be effected.

Figure 3:
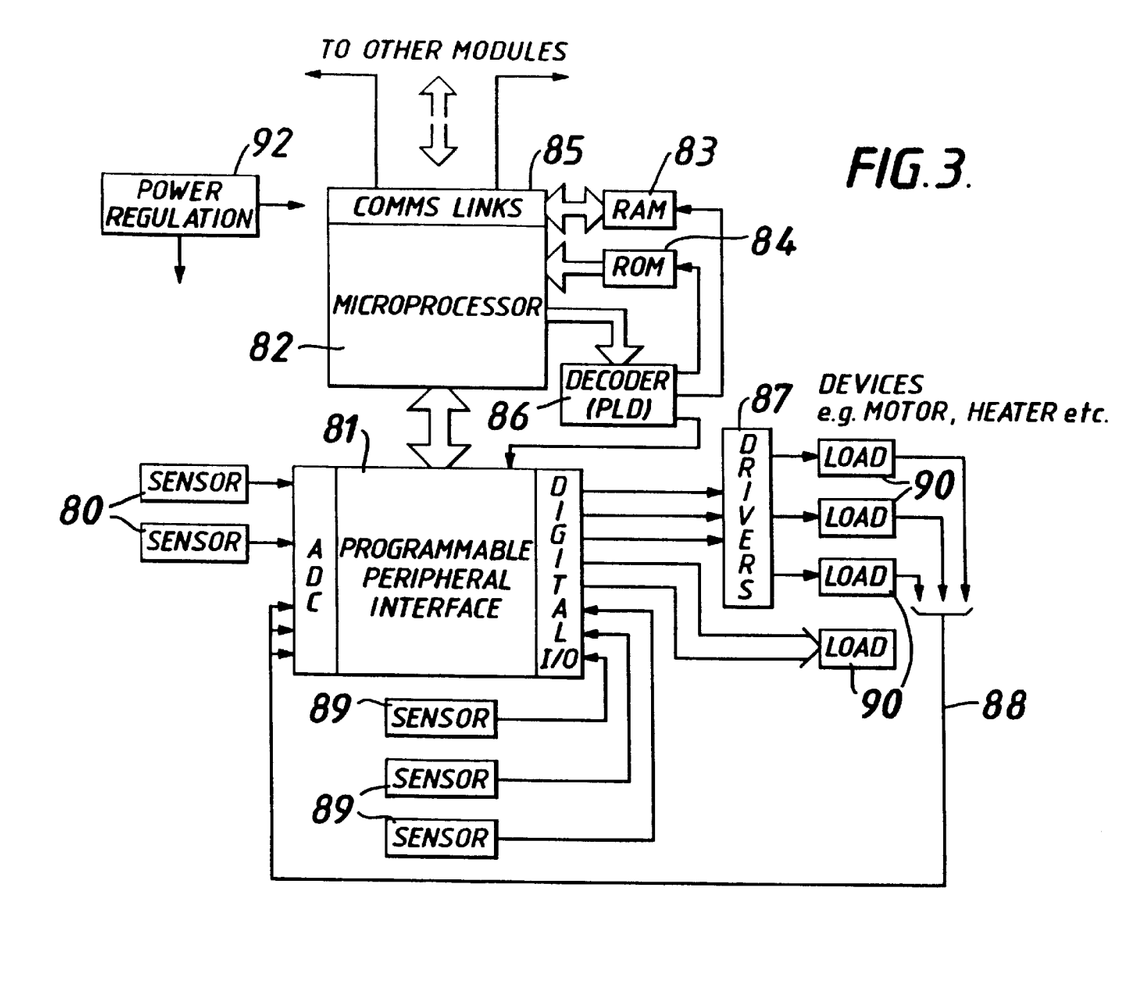
FIG. 3 shows the control mechanism associated with a module.

A master controller circuit can be located within the power module 12 and individual modules have localised control circuits to effect tasks associated with their particular devices. The master controller and the module controllers can be formed from a common approach using a hierarchial modular organisation of control and monitor process operating on independent communicating modules. The master controller is aware of operations being effected by individual modules and ensures the required tasks are carried out. Each module control arrangement includes a control board sensor and actuators of common hardware design with operation mode selection under software control. Such a module control system is shown in FIG. 3.

Analogue module sensors 80 connect to a programmable peripheral interface 81 which carries an onboard analog to digital converter (ADC) and digital I/O lines. Digital sensors 89 connect to the digital inputs. Information from the interface is made available to microprocessor 82 which includes associated data storage RAM 83 and program storage ROM 84. A communication link 85 is also available to communicate with other modules. The microprocessor accesses sensor information via interface 81 (e.g. type HD631408) and controls the loads 90, (e.g. motors or other operational devices such as heaters) via decoder 86 and driver circuits 87. Current monitoring feedback is provided via line 88. Power supply regulation block 92 ensures trouble-free power supply requirements.

The microprocessor can be a T225 transputer which contains a RISC CPU (16 bit 25 MHZ) and interprocessor communications links. Power for the devices can be high capacity nickel cadmium rechargeable batteries of the 'pancake' configuration.

The system can be sufficiently intelligent to carry out the tasks without external control although with a radio link (e.g. 1.394 GHZ) it is possible to send information on operations being effected to an 'above ground' station using the pipeline as a waveguide. Return signals could be sent to override or halt tasks if they are detected as being inappropriate. Hence automatic operation to effect an opening in the main liner would be carried out as follows.

The train of modules is driven by module 11 along the pipe until detector module 14 detects a service tee through the main liner. The aperture will typically be at the highest point in the pipe wall but the actual position is determined by the detectors. The train will then move on until the drill module 15 is at the correct position beneath the tee. The manipulator module 13 then activates its extenders 40 to clamp the module. If the drill is not determined to be in front of the aperture from earlier calculations, the module then rotates in an arc to line up the drill.

Following the drilling operation through the main liner, the manipulator module 13 retracts its extenders and the train moves forwards until the fusion module 16 is determined to be located beneath the service tee.

The manipulator module 13 again activates its extenders and clamps itself to the main pipe. A rotation of the module is effected if it is determined that this is necessary to locate the detector 70 in front of the tee. The hole already drilled in the main liner allows the service pipe liner to be inserted through the service pipe using a very flexible guide wire. The service liner has at its front end a tapered lead component formed from cross-linked polyethylene. The presence of the guide wire confirms to the detector that the correct service tee is being refurbished. Once the lead end is located in the drilled hole, the guide wire is removed, indicating that the jointing step can be effected. Thus the manipulator 13 rotates through 180° to locate the heater device 71 on the fusion module 16 adjacent to the region of the service liner end, within the main liner hole and electric power is applied to the heater to fuse the joint in the liners by raising the temperature to the crystalline melt stage, causing the service liner end-piece to expand and fuse simultaneously to the main liner.

The tasks for this service tee are now complete. The manipulator module contracts its extenders 40 and the train of modules moved on along the pipe until it detects the presence of the next service pipe, when the operations can proceed once again.

Because of the self powered, self controlled nature of the vehicle distances of 100 meters or more can be handled even with bends in the run.

Although the magnetic source for sensor module 14 may be a coil producing a field which is radial with respect to the wall of the main which is detected as falling in the region of the offtake, it is possible to use a permanent magnet arrangement as an alternative within the module.

Figure 4:
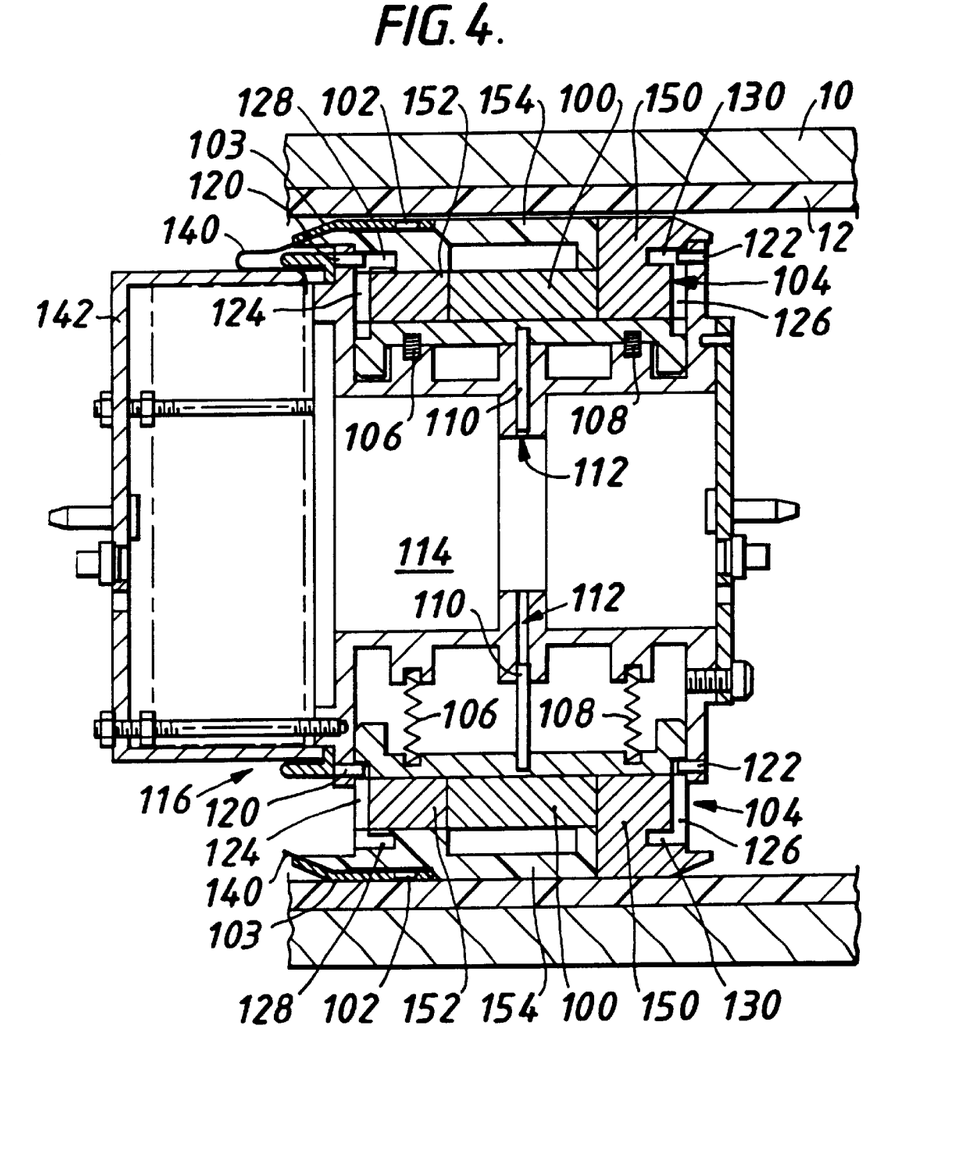
FIG. 4 shows an alternative magnetic detection module.

FIG. 4 shows such an arrangement using bar magnets 100. There is a bar magnet 100 associated with each sensor 102 (a Hall effect device having a linear output). Each sensor 102 is protected by potting compound 103. Each sensor 102 is mounted on a sledge 104 which is reciprocable radially and urged outwardly by two compression springs 106, 108. Each sledge 104 is guided by a pin 110 fixed to the sledge 104 and reciprocable in a bore 112 in a central fixed body 114.

The body 114 is part of a module 116 equivalent to module 14 of FIG. 2 which forms the train which is movable through main 1. The upper half of FIG. 4 shows a sledge 104 in its innermost position as dictated by the minimum radius which the liner 2 presents. The lower half of FIG. 4 shows a sledge 104 in its outermost position as dictated by the maximum radius which the line 12 presents. FIG. 4 is presented merely for information regarding the inward and outward movement of the sledges 104. In practice, the module 116 occupies a central position in the main. As a result, all the sledges 104 occupy similar radial positions with respect to the body 114.

Each sledge 104 is retained by pins 120, 122 fixed in the body 114 and projecting into slideways 124, 126 in the sledge 104. Each slideway 124, 126 terminates in an axially extending clearance hole 128, 130. Each sledge 104 can be removed from the body 114 by holding it in its radially innermost position, as shown in the upper half of FIG. 2 and knocking the pins 120, 122 inwardly into the clearance holes 128, 130.

Each sensor 102 has a multi-conductor lead 140 by which the sensor 102 is connected to the detector to electronics (not shown) housed in the housing 142 secured to one end of the body 114.

The magnetic lines of force generated by the bar magnet 100, in each case, leave the magnet 100 at its right-hand end and are turned radially outwardly by a block 150 of ferromagnetic material. The lines of force pass through the liner 12 and enter the cast iron main 10. The lines of force travel leftward through the main 10, then turn radially inward and pass through the liner 12, through the sensor 102 and enter another block of ferromagnetic material 152. The direction of the lines of magnetic lines of force change from radially inward to horizontal in the block 152 and then the lines of force enter the left hand end of the magnet 100.

A block 154 of plastics material bridges the gap between the two blocks 150, 152 of ferromagnetic material.

Although the magnetic source has been described as within the module, an external source could be used and can be incorporated in a probe device as an alternative which is now described with reference to FIG. 5.

Figure 5:
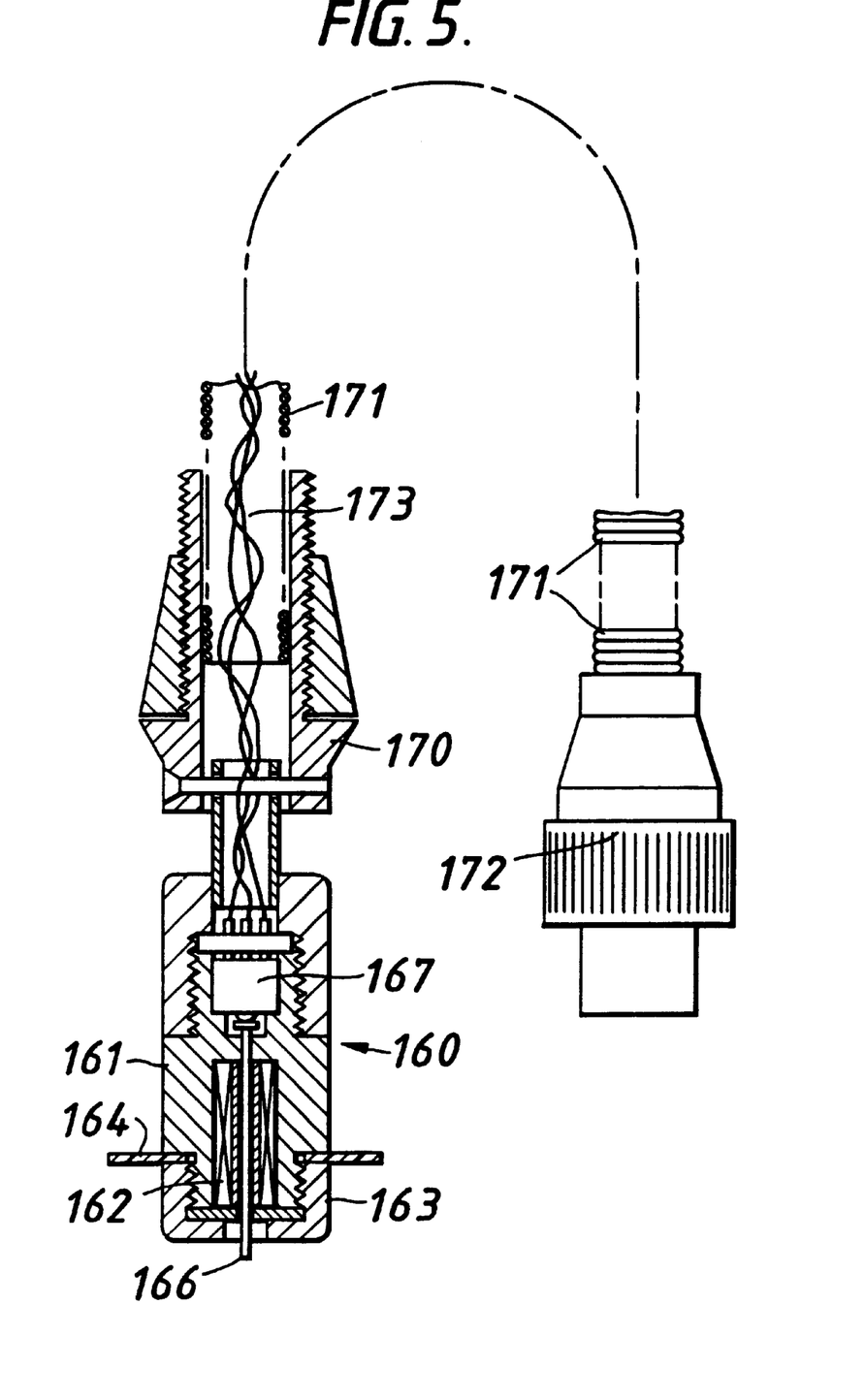
FIG. 5 shows a magnetic source probe arrangement for insertion in a service pipe.
Figure 6:
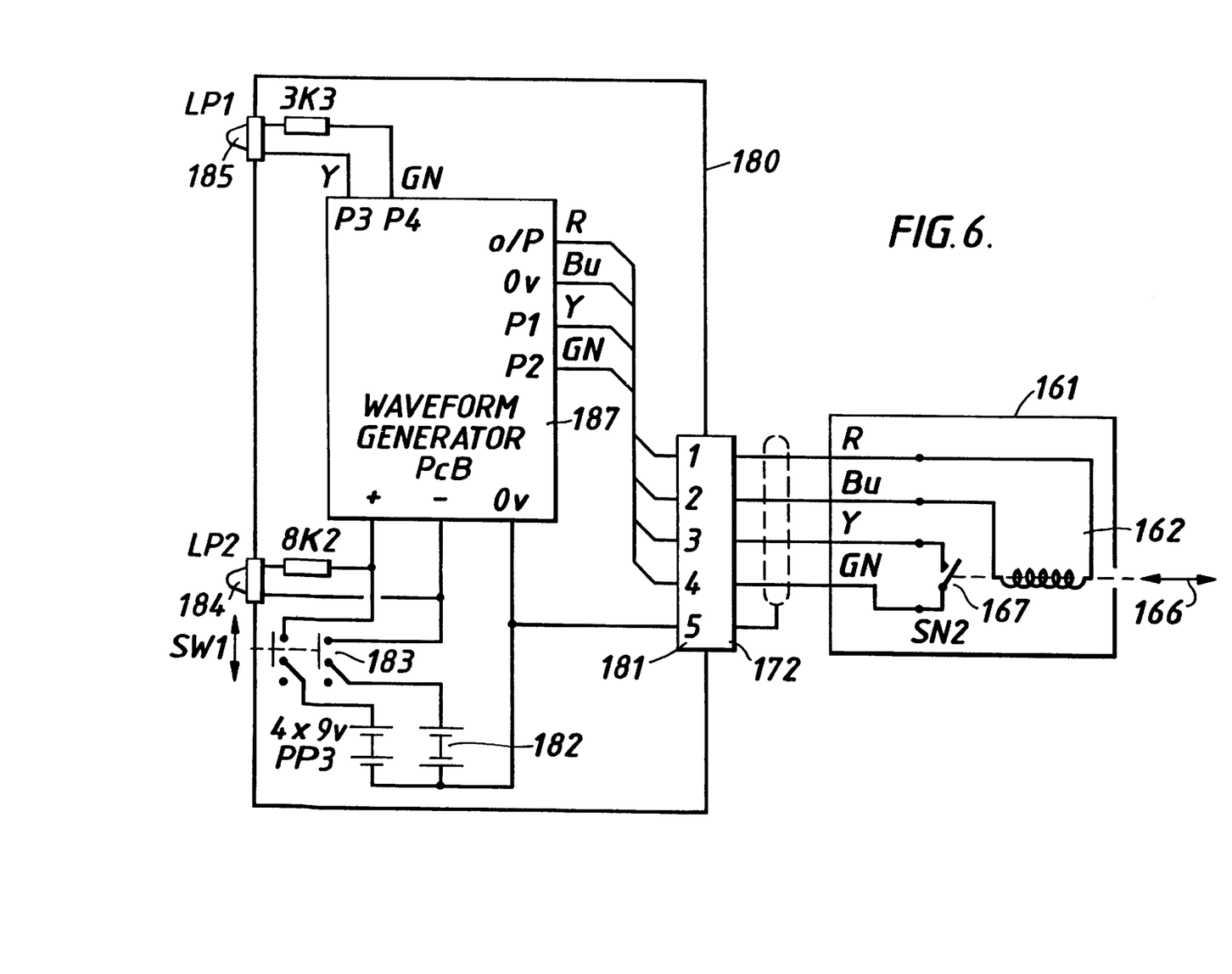
FIG. 6 shows a transmission circuit arrangement for FIG. 5.

FIG. 5 shows an elongate probe 160 including a head portion 161. The head portion includes a magnetic source coil 162 having a ferrite core and located within brass housing 163. A plastic guide washer 164 (e.g. tri-cornered PTFE) assists in guiding the probe through the service pipe. To determine when the probe is in contact with the main pipe (and more typically the main pipe liner) a switch activator 166 is provided coupled to switch 167. The head is connected to steel housing 170 to which is coupled a flexible coil-like spring tube 171 which terminates in plug 172. The hollow tube 171 carries the connecting wires 173 for the switch and coil. The tube 171 is typically about 4 meters long and is sufficiently flexible to pass through bends and other potential obstacles in the pipe. As shown in FIG. 6, the plug 172 connects with the transmission electronics within housing 180 via socket 181. The electronic circuit includes a waveform generator IC, 187 (e.g. ICL 8038) connected to a battery power source 182 via switch 183. Lamps 184 and 185 (e.g. LEDs) indicate circuit operation and when the probe contacts the main liner. Typically the generator produces an output frequency of about 35 KHz at 14 volts peak to peak.

When the probe reaches the main liner, the light 185 is illuminated and the probe is in the correct position for the in pipe vehicle to detect the ac magnetic field. Once the vehicle has detected the source, it can send a signal to the surface to allow the probe to be partially withdrawn while the drilling operation is being effected.

Figure 7:
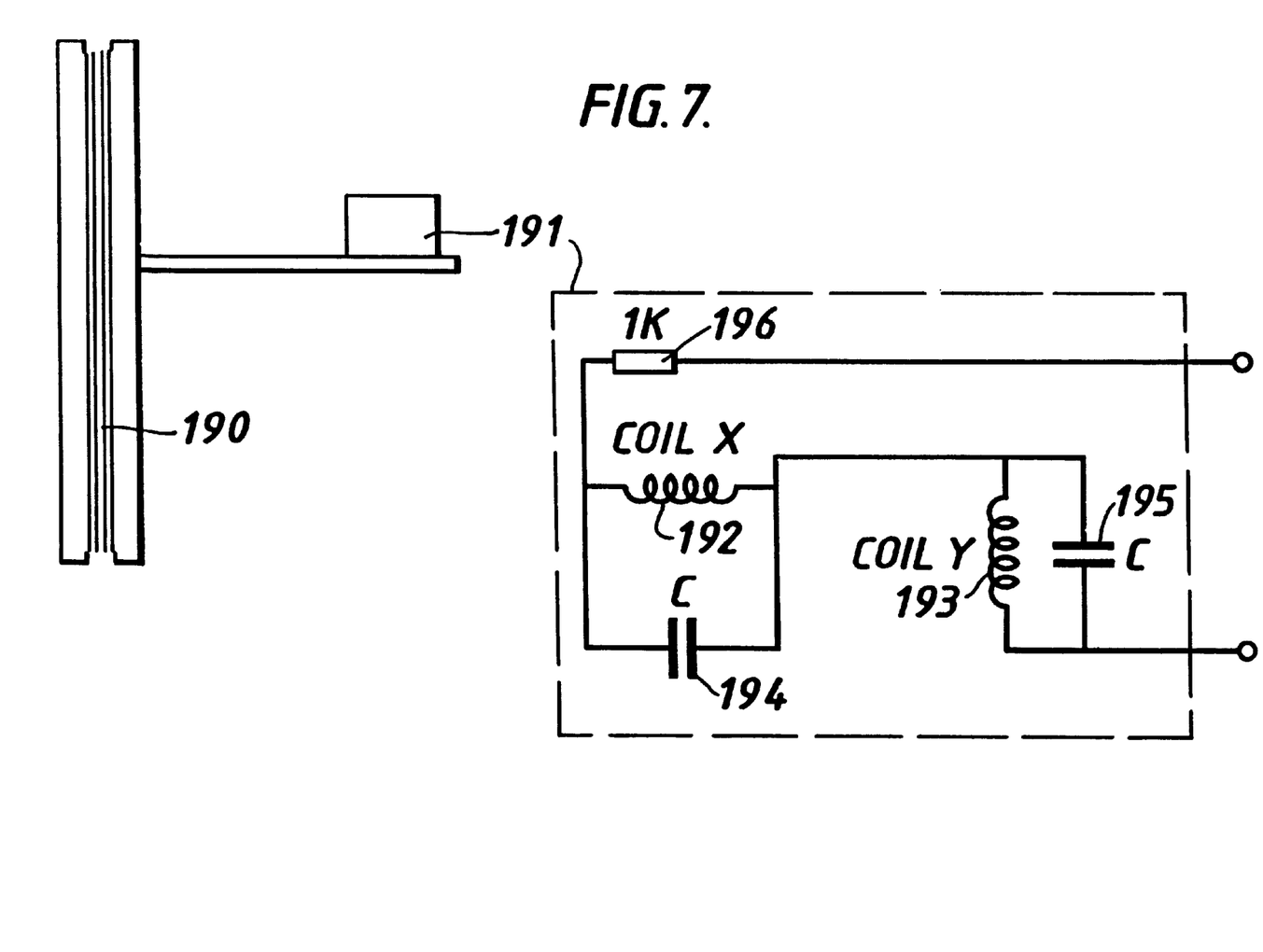
FIG. 7 shows a detector coil configuration.

The detector module 14 of the in pipe vehicle is modified to detect the source within the service pipe and can include an arrangement of the form shown in FIG. 7. It could alternatively be mounted within the drill module. The coil assembly includes a large diameter wound coil 190 which is the course position detector coil. A second fine position coil 191 assembly includes two separate windings at 90° angles to give an 'x' and 'y' co-ordinate coil 192 and 193 and associated capacitors 194, 195 and resistor 196.

Figure 8:
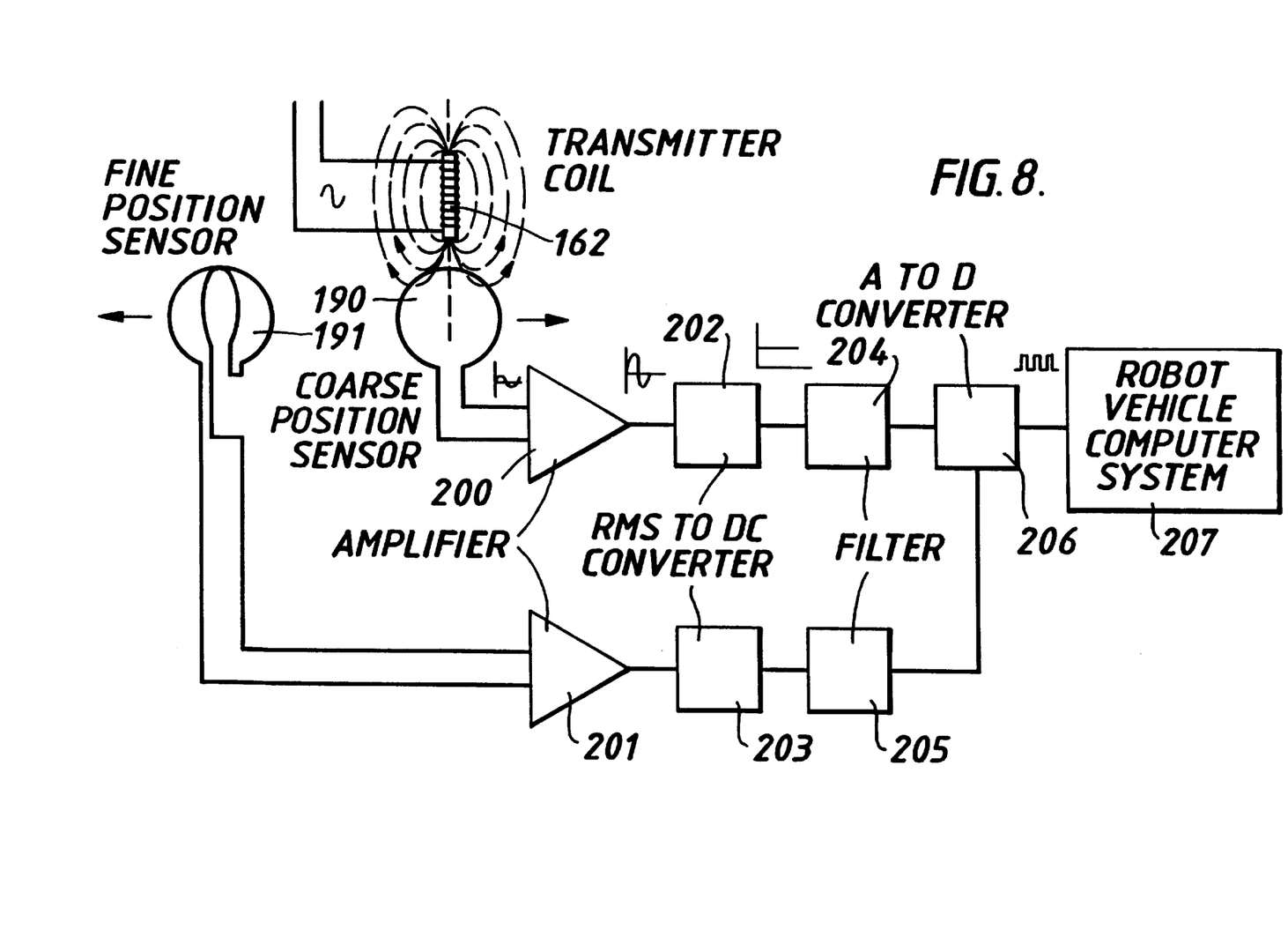
FIG. 8 shows a detector circuit arrangement for the module.

The signal field information detected by the coils 190, 191 is received by the processing circuit of FIG. 8. This circuit includes amplifiers 200 and 201 and RMS to DC converters 202, 203 and filters 204, 205. The dc outputs are converted into digital form via A to D converter 206 before handling by the vehicle computer system 207 (of the type shown in FIG. 3).

In operation, the robot is driven down the supply pipe towards the magnetic field radiated by the source located in the service tee. As the robot approaches the field, the induced voltage in the coarse coil increases and reaches a maximum as the flux cuts it at right angles. It falls to a minimum as it passes through the centre of the source and the axis of the field is in line with the coil. At this point the service tee is adjacent to the coil but it can be at any location around the circumference of the pipe. This coarse position is logged by the robot vehicle Transputer (microprocessor) and used to reposition the drill module bringing the fine coil to the same position.

When the fine coils are in the pipe section identified by the coarse coil, the Transputer initiates a search pattern, to locate the centre of the source coil. This tracks the drill module in rotational and longitudinal directions until the output from the coils is at a minimum or null.

When the fine coils are positioned at the centre of the source coil the drill module is rotated by 90 degrees which brings the drill bit in line with the centre of the source coil. The process is completed by energising the drill to cut a hole in the PE liner to take the new PE service pipe as described earlier.

The probe in the service pipe can be removed and replaced with the guide wire which carries the service pipe liner, before fusing this liner to the main pipe liner.

I claim:

1. A pipeline vehicle having a body comprising:
   a plurality of linked modules including a traction module providing drive power such that the linked modules form a self-powered train for traveling within a pipeline;
   at least one of the linked modules being capable of carrying out an operation on the pipeline;
   one of the linked modules having a detector for an item to be operated on;
   a module including a clamp that holds the vehicle at a fixed point in the pipeline;

a rotational device within another module, operable to rotate axially at least one part of the body relative to the pipeline so as to align the module capable of carrying out the operation with the item detected; and a control mechanism within the vehicle automatically controlling alignment and operation thereof in dependence on information from the detector.

2. A vehicle as recited in claim 1 wherein the traction module includes a variable drive that changes the degree of friction between the traction module and the pipeline.

3. A vehicle as recited in claim 2 wherein the detector detects a pipe junction within the pipeline.

4. A vehicle as recited in claim 3 wherein the detector includes a plurality of magnetic sensors that detect a relative circumferential position of the pipe junction within the pipeline.

5. A vehicle as recited in claim 4 wherein a magnetic source is carried within the linked module having the detector.

6. A vehicle as recited in claim 5 wherein the magnetic source includes a coil which generate a magnetic field.

7. A vehicle as recited in claim 4 wherein a magnetic source is provided externally of the linked module having the detector, said source using alternating current to generate a magnetic field.

8. A vehicle as recited in claim 1, further comprising:
a linked module that includes a drill provided to cause an aperture to be made through one of the pipeline and a lining therein.

9. A vehicle as recited in claim 1, further comprising:
a linked module that includes a heater for a plastic pipe to cause a joint to be effected between a main pipe and a smaller diameter pipe extending therefrom.

10. A vehicle as recited in claim 1, further comprising:
one linked module with an elongate cylindrical body having a first cylindrical portion configured to grip the pipeline and a second cylindrical portion coaxial therewith and configured to rotate while the first cylindrical portion grips the pipeline.

11. A vehicle as recited in claim 10 wherein a diameter of the elongate cylindrical body is no more than 150 mm.

12. A vehicle as recited in claim 1 wherein the control mechanism includes a computer device which receives an output from a plurality of sensors via an interface, said computer device being configured automatically to determine first when a pipe junction has been reached, to determine second an orientation of the pipe junction, and to determine third an amount of axial rotation and forward movement required to align the linked module capable of carrying out the operation on the pipeline.

13. A vehicle as recited in claim 12 further comprising:
a transmitter that communicates between the vehicle and a surface, said transmitter being configured to use the pipeline as a waveguide.

14. A vehicle as recited in claim 1, further comprising:
a plurality of dissimilar linked modules each being capable of carrying out a different operation on the pipeline.

15. A vehicle as recited in claim 14 wherein the plurality of dissimilar linked modules includes a module configured to detect a pipe branch, another module configured to clamp the vehicle, and a further module configured to cut through a liner within the pipeline.

16. A vehicle as recited in recited in claim 1, further comprising:
flexible links provided between the linked modules to assist in maneuvering the vehicle.

17. A vehicle as recited in claim 16, further comprising:
a plurality of wheeled intermediate modules configured to carry the flexible links.

18. A method of effecting an operation on a pipeline comprising the steps of:
passing a self-powered vehicle consisting of a train of separate flexibly linked modules including a traction module providing drive power for the vehicle through the pipeline;

detecting a presence of an item to be operated on;

then moving the vehicle to align a module with the item to carry out a desired operation;

said moving step including a substep of clamping a portion of the vehicle;

said clamping substep including a further substep of effecting axial rotational movement of the module relative to the pipeline to allow the operation on the pipeline to be automatically performed; and carrying out the desired operation automatically.

19. A method as recited in claim 18, further comprising the step of:
moving the module that carries out the operation longitudinally and axially to assist in alignment.

20. A method as recited in claim 19, further comprising the step of:
aligning a drilling module in the pipeline to effect drilling of a main pipe liner.

21. A method as recited in claim 20, further comprising the step of:
aligning a sealing module in the pipeline to seal an auxiliary pipe liner to the main pipe liner.

22. A self-powered pipeline vehicle comprising:
a traction module that provides drive power for the vehicle and that has a generally cylindrical body portion configured to move generally coaxially within a pipeline bore;

a control mechanism configured to control operation of the vehicle;

a power source which provides operational power to the vehicle;

a magnetic detector mounted on the vehicle and being capable of detecting a presence of a pipe junction in a main pipeline;

a device carried by the vehicle and configured to form an aperture in a liner within the main pipeline; and an apparatus that axially rotates the cylindrical body portion relative to the pipeline bore to align the aperture forming device with the pipe junction prior to forming the aperture at the pipe junction;

wherein said control mechanism receives information from the magnetic detector to control automatically movement of the vehicle and to control automatically formation of the aperture.

23. A vehicle as recited in claim 22 wherein the magnetic detector detects a magnetic field in a region of the pipe junction.

24. A vehicle as recited in claim 23 wherein the magnetic detector includes a course detector coil and a fine detector coil which both assist in location detection.

25. A vehicle as recited in claim 23 wherein the detector includes a magnetic source.

26. A vehicle as recited in claim 22, further comprising:
a plurality of articulated modules linked by intermediate suspension modules.

27. A vehicle as recited in claim 22, further comprising:
a sealing machine configured to seal an auxiliary pipe liner to the main liner.

28. A vehicle as recited in claim 22, further comprising:
a plurality of linked modules for serpentine movement through the pipeline.

29. A vehicle as recited in claim 22, wherein:
said control mechanism includes a computer device connected to the magnetic detector and configured to determine when the pipe junction has been reached and also to determine orientation of the pipe junction in order to control the apparatus that axially rotates the cylindrical body portion to align the aperture forming device.

30. A vehicle as recited in claim 22, further comprising:
a friction control unit that varies a degree of friction between the traction module and the pipeline.

* * * * *